United States Patent [19]

Evju

[11] 4,151,207
[45] Apr. 24, 1979

[54] PROCESS FOR PREPARATION OF 3-METHOXY-4-HYDROXYBENZALDE-HYDE

[75] Inventor: Hans Evju, Sarpsborg, Norway

[73] Assignee: Borregaard Industries Limited, Sarpsborg, Norway

[21] Appl. No.: 804,508

[22] Filed: Jun. 8, 1977

Related U.S. Application Data

[63] Continuation-in-part of Ser. No. 654,850, Feb. 3, 1976, abandoned.

[30] Foreign Application Priority Data

Feb. 10, 1975 [NO] Norway .................................. 750420

[51] Int. Cl.² ............................................... C07C 45/00
[52] U.S. Cl. ................................... 260/600 A; 210/66
[58] Field of Search ..................................... 260/600 A

[56] References Cited

FOREIGN PATENT DOCUMENTS 127545 7/1973 Norway.

OTHER PUBLICATIONS

Kirk–Othmer, Encyclopedia of Chemical Technology, 2nd ed., vol. 21 (1970) 186–190.

*Primary Examiner*—Bernard Helfin
*Attorney, Agent, or Firm*—James C. Wray

[57] ABSTRACT

A process for the production of vanillin, 3-methoxy-4-hydroxy-benzaldehyde comprising ultrafiltrating a waste sulfite liquor to obtain a concentrated lignin-rich fraction, and oxidizing said fraction by convention procedures. Advantages of the process are increased yields of vanillin and reduction or avoidance of scale formation on production equipment.

4 Claims, No Drawings

PROCESS FOR PREPARATION OF 3-METHOXY-4-HYDROXYBENZALDEHYDE

BACKGROUND OF THE INVENTION

This application is a continuation-in-part of application Ser. No. 654,850 filed Feb. 3, 1976 and now abandoned.

The present invention relates to a process for the production of 3-methoxy-4-hydroxybenzaldehyde, more commonly known as vanillin, which name will be used hereinafter.

Vanillin has been prepared industrially by the oxidation of waste liquor obtained from the sulphite cooking of cellulose. This waste liquor contains, inter alia, a substantial proportion of the lignin content of the digested wood, in the form of different derivatives thereof. By the oxidation of the waste liquor, or more particularly of the lignin component of the waste liquor, vanillin is obtained. On a dry matter basis, the waste liquor contains approximately 45% lignin, approximately 30% sugar, and approximately 25% inorganic components. By alcohol fermentation, about 60-65% of the sugar in the liquor can be removed, and such fermented waste liquor contains on a dry matter basis, approximately 55% lignin, approximately 14% sugar, and approximately 30% inorganic components.

As a raw material for the production of vanillin, fermented or non-fermented waste liquor can be used, and can be oxidized to vanillin by the process disclosed in Norwegian Pat. No. 84,422. In accordance with the process of the patent, the oxidation is effected by contacting the waste liquor, in a strongly alkaline condition, with molecular oxygen, and the reaction mixture is kept during a substantial part of the reaction period at a temperature in the range of about 100°-185° C., preferably not above 170° C. The oxygen is introduced into the reaction mixture in the form of fine bubbles of air diluted with an inert gas, and the partial pressure of oxygen in the gas mixture is kept below about 0.46 kg/cm$^2$. In such an oxidation process, it is advantageous to use an oxidation catalyst, for example a copper salt, such as copper sulphate. The process of the patent also discloses that it is advantageous to use 0.7-1.2 parts by weight of sodium hydroxide per unit weight of the dry matter in the waste liquor.

In the production of vanillin in accordance with the prior art, such as the process in Norwegian Pat. No. 84,422, it was found that there was a relatively high specific consumption of sodium hydroxide in relation to the produced weight of vanillin. Further, a substantial crust or scale is deposited in the autoclaves and also in the tube systems leading to the extraction equipment for the vanillin from the reaction mixture. The crust or scale deposited thereon comprises inorganic material. This is particularly the case when using fermented or non-fermented calcium-sulphite waste liquor. Accordingly, the production apparatus must regularly be cleaned either by washing, or, if necessary, by manual removal procedures.

Cleaning of the crust or scale from the production equipment is costly both with respect to labor and down time in production. The cleaning of the equipment results in unfavorable and undesirable interruptions in production.

BRIEF DESCRIPTION OF THE INVENTION

An object of this invention is to provide a novel process for the production of 3-methoxy-4-hydroxybenzaldehyde (vanillin).

Another object of this invention is to provide a novel process for the production of vanillin, which comprises an ultrafiltration of lignin-containing sulphite waste liquor for fractionation thereof, to obtain an enriched lignin-containing waste liquor from which vanillin can be produced by oxidation thereof.

A further object of this invention is to provide a novel process for the production of vanillin wherein the deposition of inorganic material as a scale or crust on production equipment is substantially reduced.

Briefly, the process of the invention comprises the production of vanillin from lignin-containing sulfite waste liquor, wherein the waste liquor is first subjected to ultrafiltration procedure as set forth in Norwegian Pat. No. 127,545 to obtain an enriched lignin-containing fraction. The enriched fraction is then oxidized to produce vanillin. The waste liquor used can initially be fermented to reduce the sugar content. By the process of the invention, there is a reduction or elimination in the formation of a crust or scale on the production equipment, and a higher yield of vanillin is obtained.

DETAILED DESCRIPTION OF THE INVENTION

As stated heretofore with respect to the prior art, particularly Norwegian Pat. No. 84,422, vanillin can be produced by the oxidation of fermented or non-fermented lignin-containing sulfite liquors. In accordance with this invention, the production of vanillin is produced from an enriched lignin-containing waste sulfite liquor, wherein the waste liquor has been subjected to an ultrafiltration procedure, whereby the enriched lignin-containing waste liquor fraction is obtained. The enriched fraction is then subjected to conventional oxidation procedures to produce the vanillin. It was found that the use of enriched waste liquor fraction in the vanillin production surprisingly reduces or eliminates the formation of scale or crust on the production equipment. Furthermore, it was also found that in production equipment already containing scale or crust deposited in using prior art procedures for vanillin production, the scale or crust will disappear when in the same equipment, ultrafiltrated lignin-enriched waste liquor is used.

The ultrafiltration procedures used for treatment of the fermented or non-fermented waste liquors are those set forth in Norwegian Pat. No. 127,545. Procedures set forth therein as applied to waste liquors will produce a relatively pure lignin-containing waste liquor fraction. The ultrafiltration of the waste liquors is with respect to the fractionation of the various molecular weights of the components.

The tests have shown that a higher vanillin yield can be obtained by using an ultrafiltered fraction containing lower-molecular weight lignin compounds. However, in industrial production it is not economical to manufacture vanillin from a specific lignin-containing fraction of the ultrafiltrated sulphite waste liquor, because from a practical point of view it is more advantageous to carry out the ultrafiltration to the point in which a lignin-enriched fraction is obtained, which in substance is devoid of other low-molecular weight components, such as sugar, inorganic compounds, etc.

Ultrafiltration of the waste liquor performed in accordance with the process of Norwegian Pat. No. 127,545 utilizes membranes adapted to retain a specified average molecular weight fraction. By effecting the filtration in two or more steps, and by the use of suitable membranes, it is possible to isolate the molecular weight fractions of the lignin which gives the highest vanillin yield based on the lignin, namely the lower molecular weight fractions.

By the use of the process according to the instant invention, i.e., first the ultrafiltration of the waste liquor and the subsequent oxidation of the thus obtained, relatively pure, concentrated lignin fractions, a further advantage is obtained, namely that the production of vanillin per autoclave unit will increase, the specific consumption of sodium hydroxide will decrease, and as previously mentioned, the autoclave and production equipment will substantially be devoid of crust. Thus, the cleaning of the equipment can at least be partly eliminated.

Briefly, the Norwegian Pat. No. 127,545 describes a method for the multistep fractionation and concentration of sulfite waste liquor. The method involves a combination of ultrafiltration and reverse osmosis. Thus, a measured amount of sulfite waste liquor is ultrafiltrated by enforced circulation over membranes adapted at predetermined pressures and temperatures to retain higher molecular weight fractions on the primary side. The filtrate on the secondary side of the membrane is collected and serves as a raw material for obtaining fractions having a lower molecular weight by reverse osmosis during enforced circulation through another membrane. By the use of successively finer porosity membranes an enriched, concentrated lower molecular weight, lignin-containing fraction is obtained. The procedures set forth in Norwegian Pat. No. 127,545, with respect to ultrafiltration of the sulfite waste liquor, are those used for the practice of this invention and are incorporated herein by reference.

With reference to the Norwegian Pat. No. 127,545 the following is an exerpt from the patent disclosing details pertinent to the practice of the present invention. The process according to the invention set forth in Norwegian Pat. No. 127,545 can be carried out continuously or batchwise and is explained with reference to the annexed three sheets of schematic drawings showing a device for a batchwise embodiment of the invention. FIG. 1 shows a fractionating unit. FIG. 2 shows a battery for separating various fractions, and FIG. 3 shows the means for washing the retained fractions.

With reference to FIG. 1 the sulfite waste liquor flows from the liquor tank 1 through the high pressure circulation pump 2 and a high velocity over the membrane faces 3, whereby the concentrating polarization of the membranes is reduced, and low molecular components and water pass through the membranes to their secondary side. The secondary side communicates with the atmosphere through the discharge pipe 4 for passage of the filtrate or permeate and the discharge pipe leads to the filtrate tank 5 wherein filtrate is collected for the next treatment step. The remaining portion of the sulfite waste liquor is passed through an agitator 6 and pressure regulator 7 back to the liquor tank 1. This fraction is enriched with high molecular components. The recirculation of this fraction is continued until concentration is so increased that the viscosity and osmotic pressure of the liquid is such that the filtration capacity is very low. This will take place when the recirculating liquid has a concentration of solids of 25–35%, corresponding to approximately 55–75% of the content of solids in the originally supplied liquor. If desired, this fraction can be washed with water during another circulation through the apparatus by use of the same membranes with a continuous water supply. The residual low molecular components will then be removed with the filtrate and the product obtained is pure high molecular lignosulfonate. The purity may be adjusted according to the washing time.

The filtrate, as well as concentrated filtrate from the washing operation, discharged through the pipe 4, may in turn be concentrated and subjected to further fractionating to lignosulfonate with lower molecular weight in the same manner as stated above, by use of finer membranes 3. The production of pure low molecular lignosulfonates is carried out in the same manner as described in connection with the high molecular components.

When high and low molecular lignosulfonates have been separated, a liquid remains containing sugars and salts of the waste liquor components. These cannot be separated by membranes due to too small a difference in their molecular weight, but must be separated chemically, or e.g., by prefermentation.

In FIG. 2 a battery of membranes is shown for use in a continuous process according to the invention. The separate parts have the same reference symbols as in FIG. 1 but with an added index. Thus, the membranes 3 are coarse-pored, the membranes 3a have medium porosity, and the membranes 3c are fine-pored. The filtrate tanks 5a and 5b respectively in their respective steps correspond to the liquor tank 1 of FIG. 1.

In FIG. 3, 10 is a module for ultrafiltration or reverse osmosis, 11 is a circulation tank, 12 a circulation pump, 13 a collecting pipe for permeate or filtrate discharge, 14 is a pressure regulator, 14 a level controlled valve for supply of washing water to the concentrate, 16 is a float for level control, 17 is a thermostat mixer for wash water for the concentrate, 18 a supply for cold water, 19 a supply for hot water, 20 a supply for liquor, filtrated and tempered, 21 a discharge for washed concentrate, 22 an insulation, 23 is a supply for washing water to the membranes, 24 a discharge for washing water from the membranes, and 25 and 26 are valves.

The liquor to be fractionated is introduced into the tank 11, which is insulated by a cover and an exterior insulation. In this circulation tank a float 16 is arranged for level control. The liquor leaves the tank 11 through the circulation pump 12 and is introduced into the arrangement or module 10 for ultrafiltration or reversed osmosis at the levels indicated by arrows. The liquor passing the membrane that is indicated by dotted lines, flows through the pressure regulator 14 back to the circulating tank 11, whereas the filtrate or permeate is removed through a collecting agitator 13 to be supplied to the tank for the next fractionating step.

When permeate leaves the unit 10 the level in the circulation tank 11 is reduced. When the level in this tank reaches the dotted line, the level valve 15 is opened for supply of washing water to the concentrate. The supplied washing water is tempered, partly consisting of hot water supplied through the pipe 19 and partly consisting of cold water supplied through the pipe 18. In the thermostat mixer 17, the water supply is tempered to the desired temperature. During washing operations, the level in the circulation tank is controlled by the float 16 and maintains the level indicated by the dotted line.

The ready washed concentrate is tapped through the pipe 21, whereupon the tank 11 is filled with a new batch of liquor.

To clean the membranes, washing water is supplied through the pipe 23, while valves 25 and 26 are closed. The washing water passes through the circulation 23, 12, 10 and 14 and is discharged through the pipe 24.

The following Examples illustrate the process according to this invention. A calcium sulfite waste liquor was used as a raw material and was obtained by the cellulose production from spruce and is referred to in the following as the basis liquor. In the Examples 1–3, the ultrafiltration procedures set forth above and in the Norwegian Pat. No. 127,545 were used to obtain the low molecular weight lignin-enriched, concentrated, fractions of the waste liquor.

The comparative Examples A and B illustrate vanillin production from said basis liquor, and in which the basis liquor was used without ultrafiltration. The autoclave used for the vanillin production was of the type described in FIG. 1 of Norwegian Pat. No. 84,422. In the following examples, the term "filtrate concentrate" means the fraction retained on the membrane.

EXAMPLE A

The autoclave was filled to 40% of its capacity by a waste liquor which per part by weight of dry matter in the above-mentioned basis liquor contained 7 parts by weight of water, 0.8 parts by weight of sodium hydroxide, and 0.0167 parts by weight of copper sulphate pentahydrate. The autoclave was then closed and the oxidation effected such as described in Example 2 of Norwegian Pat. No. 84,422. The obtained yield of vanillin was 6.1% based on the dry matter in the waste liquor, corresponding to 13.5% on the lignin basis.

EXAMPLE B

In this test a basis liquor was used which had been submitted to alcohol fermentation and the autoclave was filled to approximately 40% of its capacity by a waste liquor which per part by weight of the dry matter in the alcohol fermented basis liquor contained 7 parts by weight of water, 0.8 part by weight of sodium hydroxide and 0.0167 part by weight of copper sulphate pentahydrate. The liquid was oxidized as described in Example A and the obtained yield of vanillin was 7.5% based on the dry matter in the fermented waste liquor, corresponding to 13.6% based on the lignin.

EXAMPLE 1

The above-mentioned basis waste liquor was submitted to ultrafiltration in which there was used a membrane, the molecular weight separating limit of which was approximately 6,000, whereby the low-molecular weight matter in the waste liquor was removed. The thus obtained concentrate contained 49.5% of the dry matter in the basis liquor, and the dry matter of the concentrate contained 74% lignin. The obtained, lignin-enriched concentrate was used for preparation of vanillin. The autoclave was filled to approximately 40% of its capacity with a waste liquor which per weight unit of dry matter of the obtained concentrate contained 7 parts by weight of water, 0.8 parts by weight sodium hydroxide, and 0.0167 parts by weight of copper sulphate pentahydrate, and the liquid was oxidized as described in Example A. The vanillin yield was 9.8% based on the dry matter in the concentrate, which is approximately 31% higher than the yield obtained by the use of fermented waste liquor, and on a lignin basis the yield was 13.3%.

EXAMPLE 2

The above-mentioned basis waste liquor was submitted to ultrafiltration in such a way that dry matter with a molecular weight lower than 65,000 was removed as filtrate. The obtained filtrate concentrate contained 23% of the dry matter in the basis liquor and the dry matter in the obtained filtrate concentrate contained 75.5% lignin, with a molecular weight higher than approximately 65,000. The obtained filtrate concentrate was used for the production of vanillin in accordance with Example A, and the weight ratios between the dry matter of the reaction liquid, water, sodium hydroxide and the catalyst were as described in the previous Examples. The vanillin yield was 9% based on the dry matter in the concentrate, which corresponds to a yield of 11.9% calculated on the lignin.

EXAMPLE 3

The basis liquor was ultrafiltrated in two steps, in that in the first step utilized membranes with a molecular weight separating limit of approximately 65,000. The filtrate from the first step, containing dry matter with a molecular weight lower than 65,000 was in the subsequent step ultrafiltrated by using membranes with a molecular weight separating limit of approximately 6,000. The concentrate from the second step thus contained dry matter with molecular weights in the range 6,000–65,000.

The dry matter of the obtained filtrate concentrate comprised 25.5% of the dry matter in the basis liquor and the lignin content of the dry matter was 72%. The concentrate was used for the production of vanillin by the process in accordance with the previous Examples and in which the ratio between the dry matter, water, sodium hydroxide and catalyst in the reaction medium was as previously disclosed. The vanillin yield calculated on the dry matter in said concentrate was 10.7%, which is 9.2% higher than the yield obtained according to Example 1, and 43% higher than the yield obtained by the oxidation of the fermented waste liquor in accordance with Example B. On a lignin basis the vanillin yield was 14.9%.

As is apparent from the above Examples, a substantial increase in vanillin yield is obtained in accordance with the instant process calculated on the dry matter content of the reaction medium submitted to air oxidation, in consequence of which several improvements are obtained. These include a substantially higher yield per volume of the autoclave, and a substantially higher yield in the relation to the used amount of sodium hydroxide. This is of great importance because approximately 75% of the chemical costs according to the prior art procedures is accounted for by the sodium hydroxide. By comparing Example B and Example 3 it will be apparent that the increase in yield, based on the dry matter in the reaction liquir is above 40%. In both Examples the same amount of sodium hydroxide is used, and an increase in yield of vanillin of more than 40% based on the sodium hydroxide is obtained in accordance with the new process. This represents a substantial economic advantage and improvement.

As previously mentioned, by the instant process the further advantage is obtained in that the problem relating to deposition of scale or crust in the autoclaves and attendant equipment is completely or partly eliminated.

This is of great importance in the industrial production of vanillin in that the cleaning expenses in this connection are fully or partly eliminated, down time in the production of vanillin is avoided, and a continuous process is assured. It is believed that the effective production time can be increased by about 5-10% by utilization of the process of this invention.

From the foregoing description, one skilled in the art can easily ascertain the essential characteristics of this invention, and without departing from the spirit and the scope thereof, can make various changes and modifications of the invention to adapt it to various usages and conditions.

What is claimed is:

1. In the process for the production of vanillin by the oxidation of a strongly alkaline lignin-containing waste sulfite liquor and wherein scale is deposited, the improvement comprising the steps of ultrafiltrating said waste liquor, obtaining an enriched lignin-containing fraction having a molecular weight above about 1000 and devoid of other low-molecular weight components, adding an alkaline compound to said enriched fraction to obtain a strongly alkaline enriched fraction, passing oxygen through said enriched fraction at a temperature of about 100°-185° C. to oxidize said enriched fraction, and recovering vanillin from said oxidized fraction, whereby scale deposition is substantially eliminated.

2. The process of claim 1, wherein the lignin content of said waste liquor prior to oxidation is enriched with lignin by ultrafiltrating said liquor with a filter membrane which retains compounds having a molecular weight above 1,000.

3. The process of claim 1, wherein the lignin content of said waste liquor prior to oxidation is enriched with lignin by ultrafiltrating said liquor with a filter membrane which retains compounds having a molecular weight above 65,000.

4. The process of claim 1, wherein said waste liquor prior to oxidation is enriched with lignin having a molecular weight in the range of 1,000-65,000 by ultrafiltrating said liquor with a filter membrane.

* * * * *